US011906107B2

(12) United States Patent
Vath et al.

(10) Patent No.: US 11,906,107 B2
(45) Date of Patent: Feb. 20, 2024

(54) CONTINUOUS PROVISION OF A VALID LUBRICANT SAMPLE

(71) Applicant: ZF Friedrichshafen AG, Friedrichshafen (DE)

(72) Inventors: Andreas Vath, Leidersbach (DE); Guenter Berger, Castrop-Rauxel (DE); Georg Tenckhoff, Friedrichshafen (DE)

(73) Assignee: ZF FRIEDRICHSHAFEN AG, Friedrichshafen (DE)

( * ) Notice: Subject to any disclaimer, the term of this patent is extended or adjusted under 35 U.S.C. 154(b) by 477 days.

(21) Appl. No.: 17/257,321

(22) PCT Filed: Jun. 3, 2019

(86) PCT No.: PCT/EP2019/064283
§ 371 (c)(1),
(2) Date: Dec. 31, 2020

(87) PCT Pub. No.: WO2020/007545
PCT Pub. Date: Jan. 9, 2020

(65) Prior Publication Data

US 2021/0285601 A1 Sep. 16, 2021

(30) Foreign Application Priority Data

Jul. 6, 2018 (DE) ........................ 10 2018 211 164
Nov. 29, 2018 (DE) ........................ 10 2018 220 584

(51) Int. Cl.
*F16N 7/38* (2006.01)
*G01N 33/28* (2006.01)
(Continued)

(52) U.S. Cl.
CPC ............... *F16N 29/02* (2013.01); *F16N 7/38* (2013.01); *F16N 39/06* (2013.01); *G01N 1/2035* (2013.01);
(Continued)

(58) Field of Classification Search
CPC .................. F16N 2250/50; F16N 7/38; G01N 2001/2064; G01N 33/30; G01N 1/20; G01N 1/2035; G01N 2001/205
See application file for complete search history.

(56) References Cited

U.S. PATENT DOCUMENTS 4,649,711 A 3/1987 Sibley et al.
5,987,975 A * 11/1999 Rafei ..................... F16N 29/04 123/196 S (Continued)

FOREIGN PATENT DOCUMENTS

CN 202002822 U 10/2011
CN 104141515 A 11/2014

(Continued)

*Primary Examiner* — Michael R Mansen
*Assistant Examiner* — Mark K Buse
(74) *Attorney, Agent, or Firm* — LEYDIG, VOIT & MAYER, LTD.

(57) ABSTRACT

An arrangement forming a lubricant circuit includes at least one lubricant line, at least one line branching that branches the lubricant line into a first branch and a second branch. The arrangement further includes at least one lubricant reservoir integrated into the first branch, and at least one line junction where the first branch and the second branch merge. The first branch is lockable and releasable.

10 Claims, 1 Drawing Sheet

101 117 121 119
118
115
111
107
105
113 109 103

(51) Int. Cl.
*F16N 29/02* (2006.01)
*F16N 39/06* (2006.01)
*G01N 1/20* (2006.01)

(52) U.S. Cl.
CPC ...... *G01N 33/2888* (2013.01); *F16N 2200/10* (2013.01); *F16N 2250/08* (2013.01); *F16N 2250/50* (2013.01); *F16N 2270/70* (2013.01); *F16N 2280/00* (2013.01); *G01N 2001/205* (2013.01); *G01N 2001/2064* (2013.01)

(56) References Cited

U.S. PATENT DOCUMENTS

2009/0229383 A1 9/2009 Schmidt
2010/0056315 A1* 3/2010 Scholte-Wassink .... F03D 80/50 700/282
2011/0284473 A1 11/2011 Kemper
2013/0183138 A1* 7/2013 Johnson .................. F03D 80/70 415/110
2014/0324361 A1 10/2014 O'Donnell et al.
2016/0054288 A1 2/2016 O'Donnell
2017/0059031 A1 3/2017 Doertoluk et al.
2018/0252127 A1* 9/2018 Rasmussen .............. F01M 1/10

FOREIGN PATENT DOCUMENTS

CN 106199210 A 12/2016
CN 205841712 U 12/2016
DE 374396 C 4/1923
DE 4015782 A 11/1990
DE 102005053417 A1 5/2007
DE 102006049349 A1 4/2008
DE 102010004917 A1 7/2011
DE 102014002869 A1 1/2015
DE 102015113306 A1 4/2016
DE 202016103432 U1 6/2017
GB 1501903 A 2/1978
WO WO 0032980 A1 6/2000
WO WO 2017062273 A1 4/2017
WO WO 2018085875 A1 5/2018

* cited by examiner

CONTINUOUS PROVISION OF A VALID LUBRICANT SAMPLE

CROSS REFERENCE TO RELATED APPLICATIONS

This application is a U.S. National Phase Application under 35 U.S.C. § 371 of International Application No. PCT/EP2019/064283, filed on Jun. 3, 2019, and claims benefit to German Patent Application Nos. DE 10 2018 220 584.1, filed on Nov. 29, 2018 and DE 10 2018 211 164.2, filed on Jul. 6, 2018. The International Application was published in German on Jan. 9, 2020 as WO 2020/007545 under PCT Article 21(2).

FIELD

The disclosure relates to an arrangement forming a lubricant circuit and to a method for continuous provision of a valid lubricant sample using an arrangement.

BACKGROUND

In many technical systems, it is necessary to check the state of the lubricant at regular time intervals. Oil samples are taken for this purpose. In order to have this information on the state of the system, they must be taken from a flowed-through region when the system has reached its operating temperature. Such an oil sample is called valid.

The taking of oil samples is often limited. The reasons for this are, for example, poor accessibility or safety aspects. One example of a poorly accessible technical system is a wind turbine. To take an oil sample, a fitter must climb the tower of the wind turbine and manually open the gearbox.

Publication WO 2017/062273 A1 discloses a container which can be filled with lubricant via a switchable valve. A lubricant sample can be obtained by means of the container. Lubricant with which the container has been filled remains in the container until the container has been removed manually. Without manual removal, it is not possible to refill the container.

SUMMARY

In an embodiment, the present invention provides an arrangement forming a lubricant circuit. The arrangement includes at least one lubricant line, at least one line branching that branches the lubricant line into a first branch and a second branch, at least one lubricant reservoir integrated into the first branch, and at least one line junction where the first branch and the second branch merge. The first branch is lockable and releasable.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
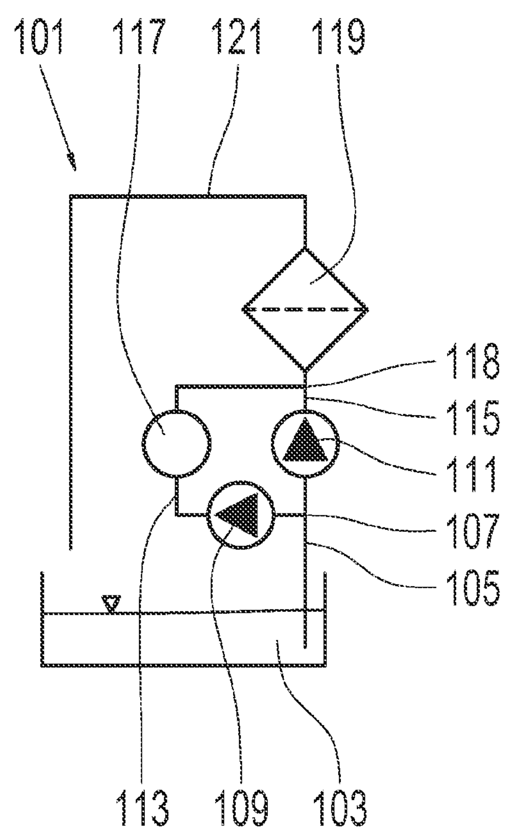
FIG. 1 illustrates a first lubricant circuit.

The present disclosure provides for improving the continuous provision of a valid oil sample. In particular, the continuous provision is to take place more flexibly, and the removal is simplified.

The present disclosure provides an arrangement having components that form a lubricant circuit. The components include a first lubricant line, at least one line branching, and at least one line junction. The line branching branches the first lubricant line. The branching results in a first branch and a second branch. Lubricant conducted from the first lubricant line is divided into a first portion and a second portion in the line branching. The first portion of the lubricant flows through the first branch, and the second portion through the second branch.

The line branching can be embodied, for example, as a node with a first terminal, a second terminal, and a third terminal. The first terminal, the second terminal, and the third terminal are connected to each other in a lubricant-conducting manner. Also, the lubricant line is connected to the first terminal in a lubricant-conducting manner; the first branch is connected to the second terminal in a lubricant-conducting manner, and the second branch is connected to the third terminal in a conducting manner.

The line junction merges the first portion of the lubricant and the second portion of the lubricant. Thus, the first portion of the lubricant and the second portion of the lubricant mix as a result of the merging. Analogously to the line branching, the line junction can be configured as a node with a first terminal, a second terminal, and a third terminal. The first terminal, the second terminal, and the third terminal are connected to each other in a lubricant-conducting manner. Furthermore, the first branch is connected to the first terminal in a lubricant-conducting manner. The second branch is connected to the second terminal in a lubricant-conducting manner. The third terminal opens into a second lubricant line and connects the latter in a lubricant-conducting manner.

According to an embodiment, at least one lubricant reservoir is provided which is integrated into the first branch. Accordingly, the first portion of the lubricant which passes through the first branch also passes through the lubricant reservoir. The lubricant reservoir is integrated into the first section such that the lubricant reservoir has a lubricant inlet and a lubricant outlet, which are integrated into the first section in a lubricant-conducting manner. By means of the lubricant inlet, the first portion of the lubricant flows into the lubricant reservoir. The first portion of the lubricant flows out of the lubricant reservoir by means of the lubricant outlet. The lubricant that has flowed into the lubricant reservoir and is located in the lubricant reservoir is available as a lubricant sample.

In order to control the filling of the lubricant reservoir, the first branch is lockable and releasable. In the locked state, the first branch is closed in a lubricant-tight manner. All lubricant then flows from the first line via the line branching through the second branch, which forms a lubricant-conducting connection between the first lubricant line and the second lubricant line. In particular, the lubricant does not flow into the lubricant reservoir when the first branch is locked.

In the released state, the first branch is lubricant-conducting. Via the first branch, a second lubricant-conducting connection then exists between the first lubricant line and the second lubricant line. In particular, the first branch is passable to the first portion of the lubricant from the line branching. This means that the first portion of the lubricant flows through the first branch when the first branch is released. The first portion of the lubricant then also flows through the lubricant reservoir, as described above.

The lubricant circuit makes it possible to release the first branch as soon as the lubricant assumes a valid state. The lubricant, which then enters the lubricant reservoir, represents a valid lubricant sample and can be removed and analyzed. In particular, it is possible to lock the first branch when the valid state of the lubricant changes. Despite the change in state, a lubricant sample, which was obtained from valid lubricant, then remains in the lubricant reservoir. In addition, the lubricant circuit makes it possible to replace a lubricant sample already present in the lubricant container—if this is not to be removed—by a newer lubricant sample.

In a preferred development, at least one valve is integrated into the first branch for locking and releasing the first branch. The valve can be opened and closed. In the closed state, the valve locks the first branch. In the open state, the valve correspondingly releases the first branch.

In a preferred development, the valve can also be integrated into the line branching or into the line junction. In this case, the valve is preferably designed as a switching valve. The switching valve selectively releases the first branch and locks the second branch, or releases the second branch and locks the first branch.

In a preferred development, the valve is temperature-controlled. This means that the valve opens or closes as a function of a temperature of the lubricant. The valve can be controlled as a function of temperature by, for example, bimetallic springs, by springs made of shape-memory alloy, by an expansion element, or, electromechanically, by means of a temperature sensor and an actuator acting on the valve.

In addition to the valve integrated into the first branch, in a preferred development, a valve is integrated into the second branch. The valve integrated into the first branch and the valve integrated into the second branch preferably open and close alternately. This means that the valve integrated into the second branch is closed when the valve integrated into the first branch is open. Conversely, the valve integrated into the second branch is open when the valve integrated into the first branch is closed. In this way, the lubricant conducted by the first lubricant line can be guided completely selectively through the first branch or the second branch.

If no valve is provided in the second branch, the lubricant flows completely through the second branch when the valve integrated into the first branch is closed. However, if this is open, a portion of the lubricant continues to flow through the second branch.

In order to convey the lubricant through the lubricant circuit, a pump integrated into the lubricant circuit is provided in a further preferred development. This is arranged upstream of the line branching or downstream of the line junction with respect to a lubricant flow running through the lubricant circuit. This means that, in the former case, the lubricant flows from the pump to the line branching. In the latter case, the lubricant flows from the line junction to the pump.

Instead of valves, pumps can also be used for controlling the lubricant flow. In a preferred development, the arrangement accordingly comprises a first pump and a second pump. The first pump is integrated into the first branch, and the second pump into the second branch. By selectively turning on the first pump and turning off the second pump, or turning on the second pump and turning off the first pump, the lubricant flow can be controlled. In the former case, the lubricant flows through the first branch and, in the latter case, through the second branch. It is also possible to switch on both pumps at the same time. In this case, the lubricant branches to one portion each on both branches.

In a further preferred development, at least one check valve is integrated into the first branch. The check valve prevents the lubricant reservoir from emptying. For this purpose, the check valve is arranged between the line branching and the lubricant reservoir with respect to a lubricant flow running through the first branch. This means that lubricant which flows from the line branching into the lubricant reservoir passes the check valve before it enters the lubricant reservoir. The check valve is oriented such that the passing lubricant is allowed through. In the opposite direction, it locks.

In a preferred development, the arrangement can have at least one lubricant filter. This is integrated into the lubricant circuit downstream of the lubricant reservoir. The lubricant filter is preferably arranged downstream of the line junction with respect to the lubricant flow running through the lubricant circuit. This means that lubricant passing the lubricant filter has previously flowed through the line junction.

A method according to the disclosure uses the arrangement or a preferred development thereof for continuous provision of a valid lubricant sample. The method provides for measuring one or more physical variables of the lubricant circulating in the lubricant circuit.

A physical variable is a quantitatively determinable property of a physical object—in the present case, of the lubricant. The temperature, the flow velocity, the volume flow, the moisture or the water content of the lubricant, and/or the time elapsed since the last switching on or the last start-up of the arrangement, for example, come into consideration as physical variables to be measured.

The method provides for controlling the valve integrated into the first branch, the valve designed as a switching valve, the valve integrated into the second branch, the first pump and/or the second pump as a function of the measured physical variables. As a result, the distribution of the lubricant on the first branch and the second branch can be influenced in a targeted manner as a function of the measured physical variables. This in turn controls the filling of the lubricant reservoir.

In a preferred development, the arrangement has at least one control unit, which is designed to carry out the method.

The lubricant circuit 101 shown in FIG. 1 comprises an oil sump 103, a first lubricant line 105, a line branching 107, a first pump 109, a second pump 111, a first branch 113, a second branch 115, a sample container 117, an oil filter 119, and a second line 121.

The oil in the lubricant circuit 101 is conveyed by means of the first pump 109 the second pump 111, or both pumps 109, 111 together. The first pump 109 is located in the first branch 113, and the second pump 111 in the second branch 115. The line branching 107 connects the first branch 113, the second branch 115, and the first line 105 to each other in a lubricant-conducting manner.

The first line 105 projects into the lubricant sump 103. In this way, the pumps 109, 111 can suck oil from the lubricant sump 103. The line junction 118 directs the oil that flows through the first branch 113 and/or the second branch 115 into the second line 121. There, it flows through the oil filter 119 arranged in the second line 121. The second line 121 transports the oil to lubrication sites, such as bearings or gears. From there, the oil flows backs to the lubricant sump 103.

After the lubricant circuit 101 is switched on, it is initially not yet possible to remove a valid oil sample due to the too low temperature of the oil. Until the oil reaches a sufficient temperature, the second pump 111 conveys the oil. The second pump 109 may be activated as needed, such as to increase the delivery rate.

Once the oil has become warm enough that a valid oil sample can be removed, the first pump 109—if it is not already—is switched on. Depending upon the dimensioning of the first pump 109 and the first branch 113, the first pump 111 can then be designed or run further. The first pump 109 conveys—when the second pump 111 continues running—a portion of the oil or—when the second pump 111 is turned off—all of the oil from the line branching 107, via the first branch 113, to the line junction 118. Since the sample container 117 is integrated into the first branch 113, it now fills with oil, which constitutes a valid oil sample.

Then, the first pump 109 is turned off. The oil now flows from the oil sump 103 through the first line 105 and the line branching 107 completely via the second branch 115. Since there is no oil in the first branch 113, no oil enters the sample container 117, such that the oil sample remains valid.

Figure 2:
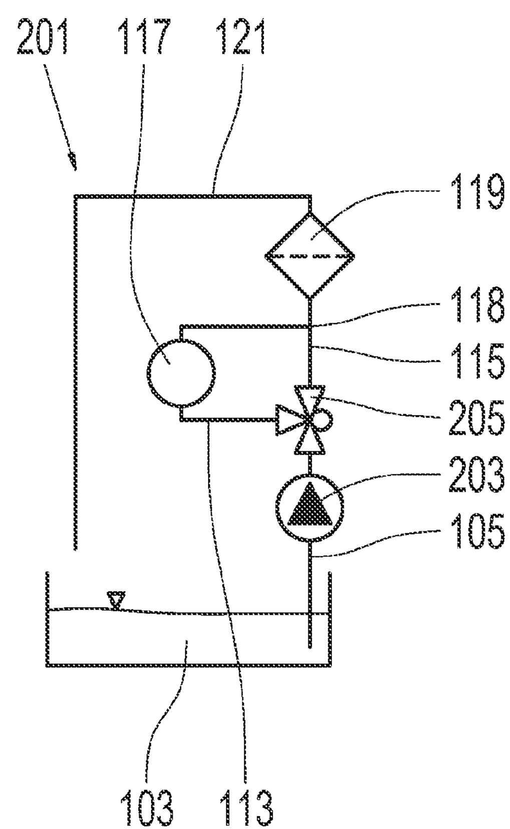
FIG. 2 illustrates a second lubricant circuit.

The lubricant circuit 201 shown in FIG. 2 differs from the lubricant circuit 101 from FIG. 1 in that only a single pump 203 is provided instead of the first pump 109 and the second pump 111. The pump 203 is located in the first line 105 and conveys oil from the oil sump 103 to the switching valve 205 via the first line 105.

In addition, a switching valve 205 replaces the line branching 107. Like the line branching 107, the switching valve 205 has a first terminal, a second terminal, and a third terminal. The first line 105 is connected to the first terminal in a lubricant-conducting manner. The second terminal is connected in a lubricant-conducting manner to the first branch 113, and the third terminal to the second branch 115.

Within the switching valve 205, there is a lubricant-conducting connection between the first terminal, the second terminal, and the third terminal. However, this connection is not static, but can be varied by actuating the switching valve 205.

If the switching valve 205 is in a first position, the first terminal and the second terminal, and thus the first line 105 and the first branch 113, are connected to one another in a lubricant-conducting manner. The third terminal, and thus the second branch 115, are thereby closed in a lubricant-tight manner. In a second position of the switching valve 205, the second terminal, and thus the first branch 113, are closed in a lubricant-tight manner, while a lubricant-conducting connection exists between the first terminal and the third terminal, and thus between the first line 105 and the second branch 115.

While subject matter of the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

101 Lubricant circuit
103 Oil sump
105 First line
107 Line branching
109 First pump
111 Second pump
113 First branch
115 Second branch
117 Sample container
118 Line junction
119 Oil filter
121 Second line
201 Lubricant circuit
203 Pump
205 Switching valve

The invention claimed is:

1. An arrangement forming a lubricant circuit, comprising:

at least one lubricant line, at least one line branching that branches the lubricant line into a first branch and a second branch, at least one lubricant reservoir integrated into the first branch;

at least one valve integrated into the first branch, wherein the valve is temperature controlled; and at least one line junction where the first branch and the second branch merge, wherein the first branch is lockable and releasable.

2. The arrangement according to claim 1, further comprising a valve integrated into the line branching or into the line junction, the valve being designed as a switching valve.

3. The arrangement according to claim 1, further comprising at least one additional valve integrated into the second branch.

4. The arrangement according to claim 1, further comprising a pump arranged upstream of the line branching or downstream of the line junction with respect to a lubricant flow running through the lubricant circuit.

5. The arrangement according to claim 1, further comprising a first pump integrated into the first branch and a second pump integrated into the second branch.

6. The arrangement according to claim 5, wherein the first pump further comprises a check valve, wherein the check valve of the pump is arranged between the line branching and the lubricant reservoir with respect to a lubricant flow running through the first branch, wherein the check valve of the pump is passable in the direction of the lubricant reservoir and locks in the direction of the line branching.

7. The arrangement according to claim 1, further comprising at least one lubricant filter, wherein the lubricant filter is arranged downstream of the line junction with respect to the lubricant flow running through the lubricant circuit.

8. A method for continuous provision of a valid lubricant sample using an arrangement according to claim 1, the method comprising:

measuring one or more physical variables of the lubricant, and controlling, as a function of the measured physical variables, a valve integrated into the first branch, a valve embodied as a switching valve, a valve integrated into the second branch, and a first pump and/or a second pump.

9. The arrangement according to claim 1, further comprising at least one controller configured to:

measure one or more physical variables of the lubricant, and control, as a function of the measured physical variables, a valve integrated into the first branch, a valve embodied as a switching valve, a valve integrated into the second branch, and a first pump and/or a second pump.

10. The arrangement according to claim 1, wherein the at least one valve actuates based on a temperature of the lubricant.

* * * * *